United States Patent
Nishino et al.

(10) Patent No.: US 10,172,581 B2
(45) Date of Patent: Jan. 8, 2019

(54) METHODS OF ASSESSING TUMOR GROWTH

(71) Applicant: Dana-Farber Cancer Institute, Inc., Boston, MA (US)

(72) Inventors: Mizuki Nishino, Newton, MA (US); Bruce E. Johnson, Brookline, MA (US); Hiroto Hatabu, Newton, MA (US); Suzanne E. Dahlberg, Chelmsford, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/917,720

(22) PCT Filed: Sep. 9, 2014

(86) PCT No.: PCT/US2014/054821
§ 371 (c)(1),
(2) Date: Mar. 9, 2016

(87) PCT Pub. No.: WO2015/035403
PCT Pub. Date: Mar. 12, 2015

(65) Prior Publication Data
US 2016/0220208 A1    Aug. 4, 2016

Related U.S. Application Data

(60) Provisional application No. 61/875,432, filed on Sep. 9, 2013.

(51) Int. Cl.
| G06K 9/00 | (2006.01) |
| A61B 6/00 | (2006.01) |
| G01N 33/574 | (2006.01) |
| A61B 6/03 | (2006.01) |
| G16H 50/20 | (2018.01) |
| G06F 19/00 | (2018.01) |

(52) U.S. Cl.
CPC .............. *A61B 6/50* (2013.01); *A61B 6/032* (2013.01); *G01N 33/574* (2013.01); *G06F 19/00* (2013.01); *G16H 50/20* (2018.01); *G01N 2800/52* (2013.01)

(58) Field of Classification Search
CPC .......... A61B 6/50; A61B 6/032; G16H 50/20; G01N 33/574; G01N 2800/52
See application file for complete search history.

(56) References Cited

U.S. PATENT DOCUMENTS

| 9,873,743 B2* | 1/2018 | Bergstein | C07K 16/2866 |
| 2004/0204435 A1* | 10/2004 | Liehr | A61K 31/4745 514/283 |
| 2008/0153853 A1* | 6/2008 | Freyne | A61K 31/4188 514/257 |

(Continued)

OTHER PUBLICATIONS

PCT search report and search opinion dated Mar. 3, 2015 for PCT/US2014/054821 is already of record and is cited as it was not included in the IDS.*

(Continued)

*Primary Examiner* — Aaron W Carter
(74) *Attorney, Agent, or Firm* — Cooley LLP; Ivor R. Elrifi; Cynthia A. Kozakiewicz (57) ABSTRACT

The present invention provides method of assessing tumor growth.

12 Claims, 4 Drawing Sheets

(56) References Cited

U.S. PATENT DOCUMENTS

| | | | | |
|---|---|---|---|---|
| 2009/0247475 | A1* | 10/2009 | Ratain | A61K 31/4545 514/23 |
| 2009/0264814 | A1* | 10/2009 | Krijnsen | A61B 5/01 604/66 |
| 2011/0166030 | A1* | 7/2011 | Wang | G01N 33/57434 506/7 |
| 2011/0223623 | A1* | 9/2011 | Serrero | C12Q 1/6886 435/7.92 |
| 2013/0084570 | A1* | 4/2013 | Hatzis | G06F 19/18 435/6.11 |
| 2013/0129168 | A1* | 5/2013 | Ross | G06T 7/0012 382/128 |
| 2016/0146781 | A2* | 5/2016 | Aneja | G01N 33/5005 424/94.5 |
| 2016/0220208 | A1* | 8/2016 | Nishino | G01N 33/574 |
| 2017/0172450 | A1* | 6/2017 | Koay | A61B 5/055 |

OTHER PUBLICATIONS

Gomez-Roca, Carlos, et al. "Tumour growth rates and RECIST criteria in early drug development." European journal of cancer 47.17 (2011): 2512-2516.*

Karrison et al., "Design of Phase II Cancer Trials Using a Continuous Endpoint of Change in Tumor Size: Application to a Study of Sorafenib and Erlotinib in Non-Small-Cell Lung Cancer", 2007.*

M Nishino et al., "Tumor volume decrease at 8 weeks is associated with longer survival in EGFR-mutant advanced non-small-cell lung cancer patients treated with EGFR TKI", *Journal of Thoracic Oncology*, vol. 8, No. 8, Aug. 1, 2013, pp. 1059-1068.

Mizuki Nishino et al., "Volumetric tumor growth in advanced non-small cell lung cancer patients with EGFR mutations during EGFR-tryosine kinase inhibitor therapy", *Cancer*, vol. 119, No. 21, Aug. 6, 2013, pp. 3761-3768.

Kikuchi Shiro et al., "Tumor volumetry: Proposal of a new concept to predict lymph node metastasis in early gastric cancer" *Anticancer Research—International Journal of Cancer Research and Treatment, International Institute of Anticancer Research*, GR, vol. 20, No. 550, Sep. 1, 2000, pp. 3669-3674.

Alexander BM et al. "Tumor volume is a prognostic factor in non-small-cell lung cancer treated with chemoradiotherapy", Int J Radiat Oncol Biol Phys., 2011, 79:1381-1387.

Arcila ME et al. "Rebiopsy of lung cancer patients with acquired resistance to EGFR inhibitors and enhanced detection of the T790M mutation using a locked nucleic acid-based assay", Clin Cancer Res. 2011, 17:1169-1180.

Castro MA, et al. "Gompertzian growth pattern correlated with phenotypic organization of colon carcinoma, malignant glioma and non-small cell lung carcinoma cell lines", Cell Prolif. 2003, 36:65-73.

Choi H, et al. "Correlation of computed tomography and positron emission tomography in patients with metastatic gastrointestinal stromal tumor treated at a single institution with imatinib mesylate: proposal of new computed tomography response criteria", J Clin Oncol. 2007, 25:1753-1759.

Cook, "Use and Misuse of the Receiver Operating Characteristic Curve in Risk Prediction," Circulation 2007, 115: 928-935.

Dehing-Oberije C, et al. Tumor volume combined with number of positive lymph node stations is a more important prognostic factor than TNM stage for survival of non-small-cell lung cancer patients treated with (chemo)radiotherapy, Int J Radiat Oncol Biol Phys. 2008; 70:1039-1044.

Demicheli R. et al. "An exponential-Gompertzian description of LoVo cell tumor growth from in vivo and in vitro data" Cancer Res. 1989, 49:6543-6546.

Eisenhauer EA et al. "New response evaluation criteria in solid tumors: Revised RECIST guideline (version 1.1)", Eur J Cancer. 2009, 45:228-247.

Engelman JA et al. "MET amplification leads to gefitinib resistance in lung cancer by activating ERBB3 signaling", Science, 2007; 316:1039-1043.

Gompertz B. "On the nature of the function expressive of the law of human mortality, and on a new mode of determining the value of life contingencies" Phil. Trans. R. Soc.(Lond.)1825; 115, 513, 2008.

Heon S, et al. "Development of central nervous system metastases in patients with advanced non-small cell lung cancer and somatic EGFR mutations treated with gefitinib or erlotinib" Clin Cancer Res. 2010; 16:5873-5882.

Heon S, et al. "The impact of initial gefitinib or erlotinib versus chemotherapy on central nervous system progression in advanced non-small cell lung cancer with EGFR mutations", Clin Cancer Res. 2012; 18:4406-4414.

Jackman DM, et al. "Exon 19 deletion mutations of epidermal growth factor receptor are associated with prolonged survival in non-small cell lung cancer patients treated with gefitinib or erlotinib", Clin Cancer Res. 2006; 12:3908-3914.

Jackman D. et al. "Clinical definition of acquired resistance to epidermal growth factor receptor tyrosine kinase inhibitors in non-small-cell lung cancer", J Clin Oncol. 2010; 28:357-360.

Jackman DM et al. "Phase II trial of erlotinib in chemotherapy-naïve women with advanced pulmonary adenocarcinoma", J Clin Oncol. 2009; 27:15s (suppl; abstr 8065).

Jackman DM et al. "Phase II clinical trial of chemotherapy-naïve patients > or= 70 years of age treated with erlotinib for advanced non-small-cell lung cancer", J Clin Oncol. 2007; 25:760-766.

Janne PA, et al. "Outcomes of patients with advanced nonsmall cell lung cancer treated with gefitinib (ZD1839, "Iressa") on an expanded access study", Lung Cancer. 2004; 44:221-230.

Kobayashi S. et al. "EGFR mutation and resistance of non-smallcell lung cancer to gefitinib", N Engl J Med. 2005, 352:786-792.

Kozak MM, et al. "Tumor volume as a potential imaging-based risk-stratification factor in trimodality therapy for locally advanced non-small cell lung cancer", J Thorac Oncol. 2011; 6:920-926.

Laird NM, et al. "Random-effects models for longitudinal data", Biometrics, 1982; 38:963-974.

Levy A, et al. "Tumor assessment criteria in phase I trials: beyond RECIST", J Clin Oncol. 2013; 20; 31:395.

Looney WB, et al. "Solid tumor models for the assessment of different treatment modalities: I. Radiation-induced changes in growth rate characteristics of a solid tumor model", Proc Natl Acad Sci USA, 1975; 72:2662-2666.

Looney WB, et al. "Solid tumor models for the assessment of different treatment modalities: systematics of response to radiotherapy and chemotherapy", Proc Natl Acad Sci USA, 1976; 73:818-822.

Looney WB, et al. "Solid tumor models for assessment of different treatment modalities: therapeutic strategy for sequential chemotherapy with radiotherapy", Proc Natl Acad Sci USA, 1977; 74:1983-1987.

Lynch TJ, et al. "Activating mutations in the epidermal growth factor receptor underlying responsiveness of non-small-cell lung cancer to gefitinib", N Engl J Med 2004; 350:2129-2139.

Maemondo M, et al. "Gefitinib or chemotherapy for non-small-cell lung cancer with mutated EGFR", N Engl J Med. 2010; 362:2380-2388.

Mok TS, et al. "Gefitinib or carboplatin-paclitaxel in pulmonary adenocarcinoma", N Engl J Med. 2009; 361: 947-957.

Mozley PD, et al. "Change in lung tumor volume as a biomarker of treatment response: a critical review of the evidence", Ann Oncol. 2010; 21:1751-1755.

Mozley PD, et al. "Measurement of Tumor Volumes Improves RECIST-Based Response Assessments in Advanced Lung Cancer", Transl Oncol. 2012; 5: 19-25.

Nishie K, et al. "Epidermal growth factor receptor tyrosine kinase inhibitors beyond progressive disease: a retrospective analysis for Japanese patients with activating EGFR mutations", J Thorac Oncol. 2012; 7:1722-1727.

Nishino M, et al. "Pictorial review of the new Response Evaluation Criteria in Solid Tumors: revised RECIST guideline version 1.1—What oncologists want to know and what radiologists need to know", AJR. 2010; 195: 281-289.

(56) References Cited

OTHER PUBLICATIONS

Nishino M, et al. "Personalized Tumor Response Assessment in the Era of Molecular Medicine: Cancer-specific and Therapy-specific Response Criteria to Complement Pitfalls of RECIST", AJR, 2012; 198:737-745.
Nishino M, et al. "Imaging of Lung Cancer in the Era of Molecular Medicine", Acad Radiol. 2011; 18:424-436.
Nishino M, et al. "CT Tumor volume Measurement in Advanced Non-small-cell Lung Cancer: Performance Characteristics of Emerging Clinical Tool", Academic Radiology, 2011; 18:54-62.
Norton L, et al. "Growth curve of an experimental solid tumor following radiotherapy", J Natl Cancer Inst. 1977; 58:1735-1741.
O'Marcaigh A.S. et al. "Estimating the Predictive Value of a Diagnostic Test, How to Prevent Misleading or Confusing Results," Clinical Pediatrics 1993, 32(8): 485-491.
Paez JG, et al. "EGFRmutations in lung cancer: correlation with clinical response to gefitinib therapy", Science 2004; 304:1497-1500.
Pao W, et al. "EGF receptor gene mutations are common in lung cancers from "never smokers" and are associated with sensitivity of tumors to gefitinib and erlotinib" Proc Natl Acad Sci USA 2004; 101:13306-13311.
Pao W, et al. "Acquired resistance of lung adenocarcinomas to gefitinib or erlotinib is associated with a second mutation in the EGFR kinase domain", PLoS Med. 2005; 2:e73.
Park K, et al. "Aspiration: Phase II study of continued erlotinib beyond RECIST progression in Asian patients (pts) with epidermal growth factor receptor (*EGFR*) mutation-positive non-small cell lung cancer (NSCLC)", J Clin Oncol. 2012 (suppl; abstr TPS7614).
Pepe et al, "Limitations of the Odds Ratio in Gauging the Performance of a Diagnostic, Prognostic, or Screening Marker," American Journal of Epidemiology 2004, 159 (9): 882-890.
Riely GJ, et al. "Prospective assessment of discontinuation and reinitiation of erlotinib or gefitinib in patients with acquired resistance to erlotinib or gefitinib followed by the addition of everolimus", Clin Cancer Res. 2007; 13: 5150-5155.
Rosell R, et al. "Erlotinib versus standard chemotherapy as firstline treatment for European patients with advanced EGFR mutation-positive non-smallcell lung cancer (EURTAC): a multicentre, open-label, randomised phase 3 trial", Lancet Oncol. 2012; 13:239-246.
Sequist LV, et al. "First-line gefitinib in patients with advanced non-small-cell lung cancer harboring somatic EGFR mutations", J Clin Oncol. 2008; 26:2442-2449.

Sequist LV, et al. "Genotypic and histological evolution of lung cancers acquiring resistance to EGFR inhibitors", Sci Transl Med. 2011; 23; 3:75ra26.
Shultz, "Clinical Interpretation of Laboratory Procedures," chapter 14, in Teitz "Fundamentals of Clinical Chemistry", 4th edition 1996, p. 192-199.
Stein WD, et al. "Analyzing the pivotal trial that compared sunitinib and IFN-α in renal cell carcinoma, using a method that assesses tumor regression and growth", Clin Cancer Res. 2012; 18:2374-2381.
Stein WD, et al. "Tumor regression and growth rates determined in five intramural NCI prostate cancer trials: the growth rate constant as an indicator of therapeutic efficacy", Clin Cancer Res. 2011; 17:907-917.
Therasse P, et al. "New guidelines to evaluate the response to treatment in solid tumors: European Organization for Research and Treatment of Cancer, National Cancer Institute of the United States, National Cancer Institute of Canada", J Natl Cancer Inst. 2000; 92:205-216.
van Zandwijk N, et al. "EGFR and KRAS mutations as criteria for treatment with tyrosine kinase inhibitors: retro- and prospective observations in nonsmall-cell lung cancer", Ann Oncol 2007; 18:99-103.
Wolchok JD, et al. "Guidelines for the evaluation of immune therapy activity in solid tumors: immune-related response criteria", Clin Cancer Res. 2009; 15:7412-7420.
Zhao B, et al. "Lung cancer: computerized quantification of tumor response—initial results", Radiology, 2006; 241:892-898.
Zhao B, et al. "Evaluating variability in tumor measurements from same-day repeat CT scans of patients with non-small cell lung cancer", Radiology, 2009; 252:263-272.
Zhou C, et al. "Erlotinib versus chemotherapy as first-line treatment for patients with advanced EGFR mutation-positive non-small-cell lung cancer (Optimal, CTONG-0802): a multicentre, open-label, randomised, phase 3 study", Lancet Oncol. 2011; 12:735-742.
Zweig et al., "ROC Curve Analysis: An Example Showing the Relationships Among Serum Lipid and Apolipoprotein Concentrations in Identifying Subjects With Coronory Artery Disease," Clin. Chem., 1992, 38(8): 1425-1428.
Nishino, M. et al., "Radiographic assessment and therapeutic decisions at RECIST progression in EGFR-mutant NSCLC treated with EGFR tyrosine kinase inhibitors," Lung Cancer, 79:283-288 (2013).
Nishino, M. et al., "Revised RECIST Guideline Version 1.1: What Oncologists Want to Know and What Radiologists Need to Know," AJR, 195:281-289 (2010).

\* cited by examiner

METHODS OF ASSESSING TUMOR GROWTH

RELATED APPLICATIONS

This application is a national stage application filed under 35 U.S.C. § 371, of International Application No. PCT/US2014/054821, filed Sep. 9, 2014 which claims benefit of, and priority to, U.S. Ser. No. 61/875,432 filed on Sep. 9, 2013, the contents of which are hereby incorporated by reference in its entirety.

GOVERNMENT INTEREST

This invention was made with government support under grant numbers K23CA157631, R01CA114465, and P50CA090578 awarded by the National Institutes of Health. The government has certain rights in the invention.

FIELD OF THE INVENTION

The present invention relates generally to methods of assessing tumor growth.

BACKGROUND OF THE INVENTION

Tumor response assessment has been a foundation for advances in cancer therapy. Conventionally, oncologists relied on one-dimensional size measurements based on Response Evaluation Criteria in Solid Tumors (RECIST), as a guide to define response and progression, and decide when to switch therapy. However, recent clinical observations have indicated that RECIST alone does not fully characterize response and progression in genomically-characterized patients with specific tumor types, such as melanoma, renal cell carcinoma, and lung cancer treated with targeted therapies. For example, experienced thoracic oncologists continue to treat NSCLC patients harboring EGFR mutation with EGFR-TKI for extended periods of time after progression by RECIST, because their tumors grow slowly suggesting that some tumor cells remain sensitive to erlotinib. There is a critical need for additional radiographic strategies to define response and progression of solid tumor.

SUMMARY OF THE INVENTION

The present invention relates to methods for determining tumor volume growth rate, and applications of such methods for assessing tumor progression and providing treatment recommendations.

In various aspects the invention features methods of assessing tumor growth rate in a patient by determining the tumor volume; determining the natural log ($\log_e$) of the tumor volume to provide a patient volumetric tumor growth rate; and comparing the patient volumetric growth rate to a threshold volumetric tumor growth rate. When the patient volumetric growth rate is lower than the threshold volumetric tumor growth indicates the tumor is slow growing. When the patient volumetric growth rate is higher than the threshold volumetric tumor growth indicates that the tumor is fast growing.

The invention also features methods of providing a treatment recommendation for a patient by a) determining the tumor volume at a first period of time; b) determining the natural log ($\log_e$) of the tumor volume determined in step (a) to provide a first patient volumetric tumor growth rate; c) determining the tumor volume at a second period of time; d) determining the natural log ($\log_e$) of the tumor volume determined in step (a) to provide a second patient volumetric tumor growth rate; and e) comparing the first and second patient volumetric growth rates to a threshold volumetric tumor growth. When both the first and second patient volumetric growth rates are higher than the threshold volumetric tumor growth rate indicates that the patient's treatment regimen should be altered.

The invention further provides a method of assessing the need for further prognosis tests for patient with a tumor by a) determining the tumor volume at a first period of time; b) determining the natural log ($\log_e$) of the tumor volume determined in step (a) to provide a first patient volumetric tumor growth rate; c) determining the tumor volume at a second period of time; d) determining the natural log ($\log_e$) of the tumor volume determined in step (a) to provide a second patient volumetric tumor growth rate; e) comparing the first and second patient volumetric growth rates to a threshold volumetric tumor growth, such that when both the first and second patient volumetric growth rates are lower than the threshold volumetric tumor growth rate indicates no need for additional prognostic tests.

In some embodiments, the first period of time is after the patient's tumor has reached nadir. Nadir as used herein refers to the smallest tumor volume recorded.

The invention also provides a computer implemented method that includes receiving data characterizing a growth rate of tumor volume over time of a patient having a tumor and subject to a treatment protocol; determining whether to change the treatment protocol by comparing the growth rate of the tumor over time to a predefined growth rate threshold value; and providing data characterizing whether to change the treatment protocol.

The invention also provides a computer-implemented method that includes receiving data characterizing a growth curve of tumor volume over time of a patient having a tumor and subject to a treatment protocol; comparing a slope of the growth curve to a predefined growth curve slope; determining, based on the comparison, whether to change the treatment protocol; and providing data characterizing whether to change the treatment protocol.

In any of the foregoing methods, the tumor has reached nadir prior to implementation of the method.

In any of the foregoing methods, the tumor volume tumor volume is determined radiographically. The radiographic method used may be any radiographic method known in the art. For example, the radiographic method is a CT scan.

The tumor is a solid tumor. Solid tumors may include, but are not limited to, tumors from the breast, colon, prostate, liver, kidney, pancreas, cervix, testes, ovary, brain, lung, or skin. In some embodiments, the tumor is a lung tumor.

The patient is receiving treatment for the tumor. The patient is receiving a targeted therapy for the tumor. The targeted therapy is based upon a tumor mutation. The targeted therapy is a tyrosine kinase inhibitor.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

A. The baseline CT demonstrated a dominant mass in the right lower lobe, measuring 25,016 mm$^3$.

B. The patient was treated with erlotinib. At 4 month of therapy, the tumor volume significantly decreased and reached the nadir, measuring 5,288 mm$^3$.

C. At 5 month, the tumor started to grow back and measured 7,490 mm$^3$. The growth rate of $\log_e V$ since the prior scan was 0.22/month.

D. At 7 month, the tumor volume further increased, measuring 12,922 mm$^3$. The growth rate of $\log_e V$ since the prior scan was 0.33/month. A week later, erlotinib was discontinued and the patient was subsequently treated with platinum-based chemotherapy.

A. The baseline CT demonstrated a dominant right upper lobe lesion, measuring 14,495 mm$^3$.

B. The patient was treated with gefitinib and tumor volume significantly decreased, reaching the nadir measuring 4,121 mm$^3$ at 8 months.

C-H. The tumor started to grow back with gradual increase of tumor volume over a course of 2 years (C:11 month, D:16 month, E:19 month, F:21 month, G:26 months, H:28 month of therapy). The maximum growth rate of $\log_e V$ between two consecutive scans since nadir was 0.09/month. Gefitinib was discontinued at 28 months and the patient was subsequently treated in a trial of irreversible EGFR inhibitor.

A. The baseline CT demonstrated a lung lesion with nodular pericardial thickening.

B. The patient was treated with crizotnib demonstrated marked decrease of the lesion and nodular pericardial thickening at 8 weeks.

DETAILED DESCRIPTION OF THE INVENTION

The present invention relates to a method of determining tumor volume growth rate that allows the clinician to accurately define response to therapy and disease progression. The method provides for the identification of patients whom can safely remain on a cancer therapy while their tumors grow slowly, thus maximizing the therapeutic benefit.

Imaging plays a key component in assessing response and progression during cancer therapy. Response Evaluation Criteria in Solid Tumors (RECIST), as a guide to define response and progression, and decide when to switch therapy. However, recent clinical observations have indicated that the conventional RECIST-based assessment alone does not fully characterize response and progression in genomically-characterized patients with specific tumor types, including gastrointestinal stromal tumors (GIST), melanoma, lung cancer treated with targeted therapies [19-22]. New radiographic response criteria have been proposed, such as Choi criteria for GIST utilizing CT density, and immune-related response criteria (irRC) for melanoma in which response may be observed after initial increase of tumor burden [19-22]. Thoracic oncologists continue to treat NSCLC patients harboring EGFR mutations with EGFR-TKI beyond RECIST progression, because their tumors tend to grow slowly and patients remain asymptomatic, suggesting that some tumor cells remain sensitive to TKI [23-25]. Nishie et al demonstrated continuous EGFR-TKI after progression was associated with improved overall survival compared to those who switched to chemotherapy alone [26]. EGFR-TKIs are associated with improved quality of life and less toxicity compared to chemotherapy [7-10]. The benefit of EGFR-TKI should be maximized by adequately prolonging the duration of TKI therapy. A study examined NSCLC patients harboring EGFR mutations treated with first-line TKI, in which 88% of the patients continued TKI beyond RECIST progression, indicating that RECIST progression is not the single determining factor for terminating TKI [25]. There is a clear need for additional radiographic criteria of tumor growth beyond RECIST progression to better guide therapeutic decisions.

One of the major limitations of RECIST is the use of the cut-off value of tumor size increase to define progression, which does not incorporate the changes of tumor burden over time and the tumor growth rate. Tumor volume measurement using multidetector-row CT (MDCT) has been studied to complement limitations of RECIST. Tumor volume measurements in NSCLC are feasible with higher reproducibility than size measurements [27-31]. We have previously established a CT tumor volumetry technique in advanced NSCLC using FDA approved software [31]. The study showed tumor volume is more reproducible than size, which was consistent with other studies [27-31]. The volume assessment has also been used to predict outcome in NSCLC patients treated with chemotherapy and chest radiotherapy [32-34]. In advanced NSCLC patients with sensitizing EGFR mutations, tumor volume decrease at 8 weeks of EGFR-TKI therapy is associated with longer survival [35]. However, detailed characterization of volumetric tumor growth rate in EGFR-mutant NSCLC patients after initial response to EGFR-TKI therapy has not been systematically performed.

Tumor growth is based on a specific relationship between tumor volume and time, and comprehensive equations of tumor growth have been extensively pursued in the past decades. One of the well-studied models is the Gompertzian model, which was initially described by Gompertz in 1825 to deal with human mortality and later unexpectedly found useful to describe biological tumor growth [36-38]. Tumor growth by Gompertzian model has an exponential nature at the early stage, and subsequently saturates, approaching a plateau as tumor increases [37]. While the growth of most untreated tumors has been well described by the Gompertzian equation, the growth of treated tumors presents another investigational challenge [37-39]. In late 1970 s, Looney et al quantitatively evaluated tumor growth curves in rat hepatoma during radiotherapy and chemotherapy, attempting to more precisely evaluate therapeutic effects, improve therapeutic scheduling, and better understand tumor biology [40-42].

Whether a tumor is fast growing or slow growing is an important factor in making treatment decisions in a clinical setting. However, no objective quantitative data for tumor growth rate exists. The present invention solves this problem by providing a reference value for volumetric tumor growth rate in cancer patients whereby the reference value allows the clinician to determine whether the tumor is fast growing or slow growing. Patients whose tumors are slow growing can safely remain on their current treatment protocol, whereas patients whose tumor are fast growing should change treatments.

The present study provided the volumetric tumor growth rate after the nadir in cancer patients receiving treatment. The result provides a reference value for the tumor growth rate in patients progressing on treatment, which can identify patients who can safely remain their treatment protocol. This is the first report providing a reference value of volumetric tumor growth in cancer patients treated with therapy.

The present study focused on EGFR-mutant NSCLC patients receiving tryrosine kinase inhibitor (TKI) therapy, since with was believed that the tumor growth rate and its threshold for fast versus slow growth are cohort-specific and therapy-specific. We utilized the CT tumor volume measurements, rather than tumor size. We chose this approach since we have demonstrated that tumor volume measurement is more reproducible than size measurement and detects smaller changes more accurately [31]. In addition, the prior study by our group demonstrated that tumor volume decrease at 8 weeks of EGFR-TKI therapy was associated with longer survival in EGFR-mutant advanced NSCLC patients, while tumor size was not associated with survival [35].

The initial model adjusting for time from baseline alone provided the growth rate of 0.12/months. The growth rate adjusting for time and baseline volume was also 0.12/month, indicating that the baseline volume does influence how big the tumor is at each time point after nadir, however, does not have much effect on how fast the tumor grows; the tumors in our cohort grow at an overall rate of 0.12/months for $\log_e V$ after their nadir, regardless of their baseline volume. The result is consistent with our prior observation that baseline volume was not associated with survival in EGFR-mutant NSCLC patients receiving EGFR-TKI [35]. The growth rate was also 0.12/months adjusting for clinical variables, demonstrating the stability of the model. The model and the consistency of the growth rate of 0.12/month need to be validated in a larger independent cohort of patients with sensitizing EGFR mutations treated with TKI, in order to determine if the consistent results are due to an artifact of the model fitting or truly reflect biologically-driven behavior of EGFR-mutated tumor.

Our goal was to identify a cut-off value that can differentiate patients who are slowly progressing and can safely remain on EGFR-TKI. The upper limit of the 95% CI for the rate, 0.15/months was used because it is often used to determine outliers in the tumor volume studies and in growth models [51]. We investigated the occurrence of two consecutive observations of rate >0.15/months; only one observation can be a result of measurement variability rather than true tumor change, and clinicians tend to give a "benefit of a doubt" and confirm observations on one more scan before making decisions. The concept of confirmation is well-established in RECIST, and is given more emphasis in irRC, where confirmation is required for progression [16-19].

Two consecutive events of rate >0.15/months occurred after their nadir in all 14 patients, which is reassuring. The time on TKI was shorter in these 14 patients than in 44 patients without the events, indicating that the events did not happen by chance.

While the inventors have demonstrated the utility of the methods with lung cancer, one skilled in the art would readily appreciate that the methods of the invention can be utilized on any cancer in which tumor volume can be measured Predicting the Response to Therapy The disclosed methods are useful for monitoring subjects undergoing treatments and therapies for cancer, and for selecting or modifying therapies and treatments that would be efficacious in subjects having cancer, wherein selection and use of such treatments and therapies slow the progression of the tumor, or substantially delay or prevent its onset, or reduce or prevent the incidence of tumor metastasis.

The methods disclosed herein are used with subjects undergoing treatment and/or therapies for cancer. The methods of the present invention are to be used to monitor or select a treatment regimen for a subject who has a cancer.

These methods are both a positive and negative predictive test and thus allow clinicians to better focus the use of these expensive and toxic agents to that subset of the population the greatest potential chance of benefit as early as possible.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic, predictive, or prognostic test, assay, or method concerns the ability of the test, assay, or method to distinguish between subjects responsive to chemotherapeutic treatment and those that are not, is based on whether the subjects a volumetric tumor growth rate above a pre-determined threshold.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for therapeutic unresponsiveness, and the bottom quartile comprising the group of subjects having the lowest relative risk for therapeutic unresponsiveness. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future events. Often such lower diagnostic accuracy tests must be combined with additional parameters in order to derive meaningful clinical thresholds for therapeutic intervention, as is done with the aforementioned global risk assessment indices.

A health economic utility function is yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

Computer Implemented Methods

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Other embodiments may be within the scope of the following claims.

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

A "Clinical indicator" is any physiological datum used alone or in conjunction with other data in evaluating the physiological condition of a collection of cells or of an organism. This term includes pre-clinical indicators.

"Clinical parameters" encompasses all non-sample or non-analyte biomarkers of subject health status or other characteristics, such as, without limitation, age (Age), ethnicity (RACE), gender (Sex), or family history (FamHX).

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining biomarkers are linear and non-linear equations and statistical classification analyses to determine the relationship between biomarkers detected in a subject sample and the subject's responsiveness to chemotherapy. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcomes expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the responsiveness to treatment, cancer recurrence or survival and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. "Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is considered highly significant at a p-value of 0.05 or less. Preferably, the p-value is 0.04, 0.03, 0.02, 0.01, 0.005, 0.001 or less.

A "subject" in the context of the present invention is preferably a mammal The mammal can be a human, non-human primate, mouse, rat, dog, cat, horse, or cow, but are not limited to these examples. Mammals other than humans can be advantageously used as subjects that represent animal models of cancer. A subject can be male or female.

"TN" is true negative, which for a disease state test means classifying a non-disease or normal subject correctly.

"TP" is true positive, which for a disease state test means correctly classifying a disease subject.

EXAMPLES

Example 1: General Methods

Patients

The study population included 58 patients with stage IV NSCLC (AJCC 7$^{th}$ edition) or stage I-IIIA NSCLC with systemic relapse and sensitizing EGFR mutations, treated with gefitinib or erlotinib as their initial systemic therapy for advanced NSCLC between February 2002 and May 2011 at Dana-Farber Cancer Institute. The patients had baseline CT demonstrating at least one measurable lung lesion (≥10 mm in the longest diameter) and at least two follow-up CT scans during EGFR-TKI therapy, and experienced volumetric tumor growth while on TKI. Patients provided informed consent and their records were retrospectively reviewed with IRB approval.

Table 1 summarizes the patient and disease characteristics. The median time on TKI monotherapy was 15.8 months. The median number of follow-up scans was 7.5 [range: 2-35]. The median time from baseline to tumor volume nadir was 6.3 months.

Mutation Analysis

Tumor specimens were obtained from diagnostic or surgical procedures. Samples consisted of frozen tumor specimens or paraffin embedded material. EGFR exons 18 to 21 were amplified by PCR and analyzed bidirectionally by direct sequencing for the presence of somatic mutations [1-2]. The following EGFR mutations were considered sensitizing: deletions, duplications, and deletion-insertions of exon19, L858R point mutation, L861Q point mutation, and G719 missense point mutations [25, 43-44].

Tumor Volume Measurements

Baseline and follow-up CT scans were performed to determine response to EGFR-TKI using the clinical chest CT protocol [31]. Follow-up CT scans were performed every 8 weeks for 33 patients enrolled in prospective trials of EGFR-TKI, and at the discretion of the treating providers for 25 patients treated off protocol [5,25,45-47]. A thoracic radiologist (M.N.) measured the volume of a dominant measurable lung lesion (one lesion/patient) on baseline and all CT during EGFR-TKI monotherapy, using FDA-approved volume analysis software previously validated (Vitrea® 2, Vital Images, Minnetonka, Minn.)[31]. We utilized this technique based on our previously published data of high interobserver reproducibility, which demonstrated that the tumor volume measurements are more reproducible than size measurements [31]. The nadir (the smallest tumor volume recorded from baseline to TKI termination/last follow-up) was determined for each patient.

Statistical Analysis

A total of 405 volume measurements from the nadir to the end of TKI therapy/last follow-up, with data closure on Jun. 1, 2012, were analyzed. Demographics and disease characteristics were summarized with descriptive statistics. A linear mixed effects model, fitting time as a random effect [48], was fitted to the repeated measures of volume data to estimate the effect of time and other prognostic factors on tumor growth. The tumor volume ($mm^3$) was transformed to the natural logarithm scale, and the logarithm of tumor volume ($\log_e V$) was used. The first model was built adjusting only for time in months from baseline. Since the baseline volume ($\log_e V_0$; the tumor volume measured on the baseline scan performed before the initiation of TKI therapy) may influence the tumor volume and its growth rate, the second model was adjusted for time and $\log_e V_0$. The third model was adjusted for time, $\log_e V_0$, and clinical characteristics shown in Table 1, to determine if clinical variables have significant effect on the tumor growth.

Example 2: Measurement of the Volumetric Tumor Growth Rate

Figure 1:
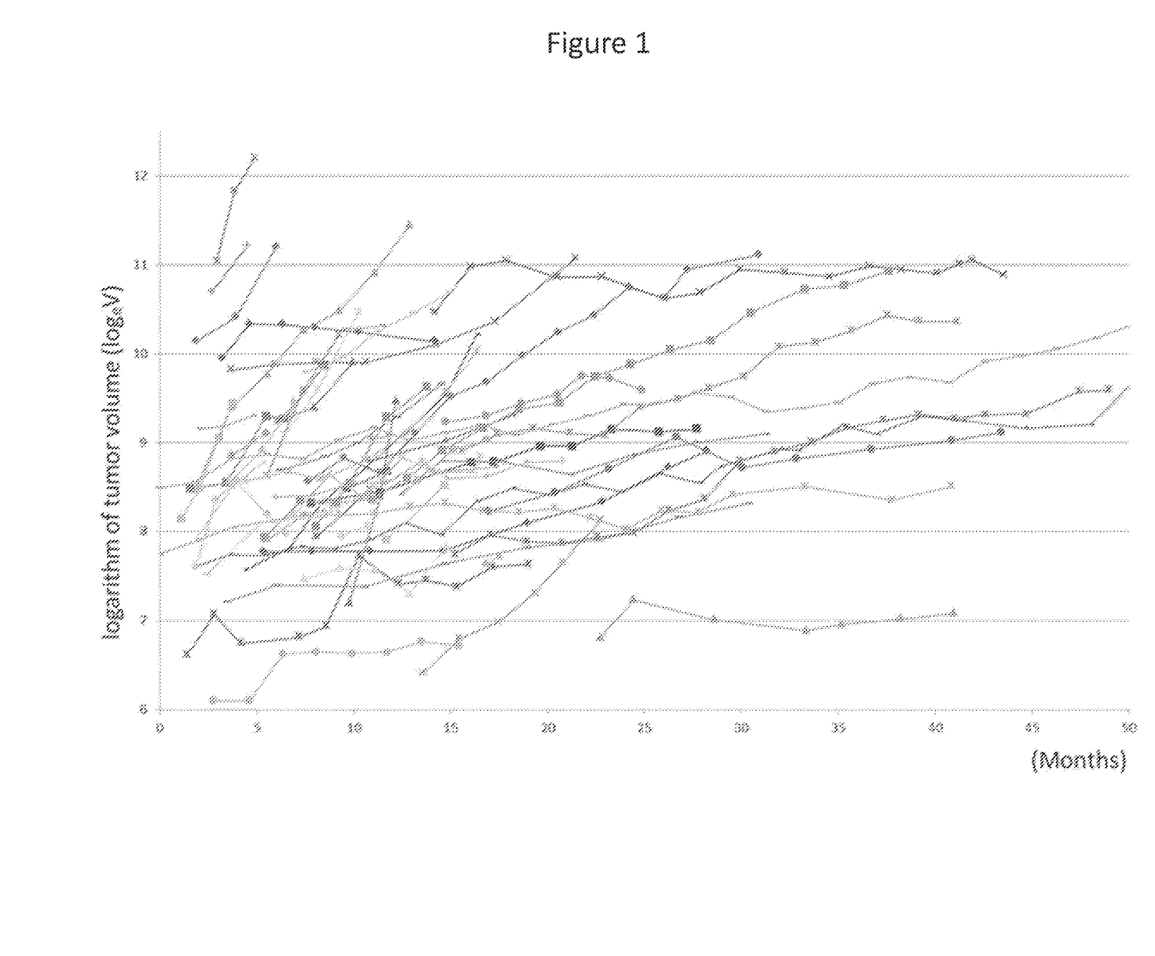
FIG. 1 Spiderplot represents volumetric tumor growth curves of the 58 patients after they reached their volume nadir.

FIG. 1 represents the volumetric tumor growth of 58 patients from their nadir to termination of therapy or the last follow-up scan. A linear mixed effects model was fitted to predict growth of $\log_e V$, adjusting for time from baseline.

In the first model, $\log_e V$ was estimated as a function of time from the baseline, and the following equation was obtained:

$$\log_e V = 0.12 * time + 7.68$$

In this equation, time represents the number of months from the baseline. The regression coefficient for time, 0.12/month, represents the growth rate of $\log_e V$ (SE:0.015; p<0.001).

The second model was adjusted for $\log_e V_0$ as a fixed effect, and $\log_e V$ was estimated as follows:

$$\log_e V = 0.12 * time + 0.72 \log_e V_0 + 0.61$$

$\log_e V_0$ was a significant predictor of the volume after the nadir (P<0.001), with the coefficient of 0.72. The growth rate of $\log_e V$, obtained as a coefficient for time, was 0.12/month (SE:0.015, P<0.001) after adjusting for $\log_e V_0$. Therefore, the growth rate is 0.12/months for $\log_e V$, regardless of the baseline volume.

In the third model adjusted for the clinical variables and $\log_e V_0$, stage at diagnosis (stage IV vs. others), TKI (gefitinib or erlotinib), and smoking status (current/former vs. never smoker) were significant predictors of the volume after the nadir, along with $\log_e V_0$ (P<0.001 for $\log_e V_0$, P=0.08 for stage, 0.04 for TKI, and 0.04 for smoking). The following equation was obtained:

$$\log_e V = 0.12 * time + 0.64 \log_e V_0 + 0.83 * stage + 1.00 * TKI + 0.54 * smoking + 0.34$$

(Stage=1 for stage IV, 0 for stage I-III; TKI=1 for gefitinib, 0 for erlotinib; smoking=1 for current/former smoker, 0 for never smoker). The growth rate of $\log_e V$ was again 0.12/month (SE: 0.01, P<0.001). Stage, TKI and smoking affect how large the tumor volume is, however, the tumor growth rate is at 0.12/months for $\log_e V$, regardless of these clinical characteristics or baseline volume.

Example 3: Determination of the Threshold for Volumetric Tumor Growth

To explore the appropriate criteria for tumor growth that can identify patients who can safely remain on EGFR-TKI, the threshold of the growth rate of $\log_e V > 0.15$/months was proposed, based on the rate obtained from the equations (0.12/month) plus twice the standard error, 0.015 (0.12+0.015×2=0.15), representing the upper 95% confidence interval for the rate. We calculated the growth rate of $\log_e V$ between 2 consecutive scans after nadir and investigated two consecutive occurrences of the growth rate of $\log_e V > 0.15$/months during EGFR-TKI therapy in the 58 patients.

Figure 2:
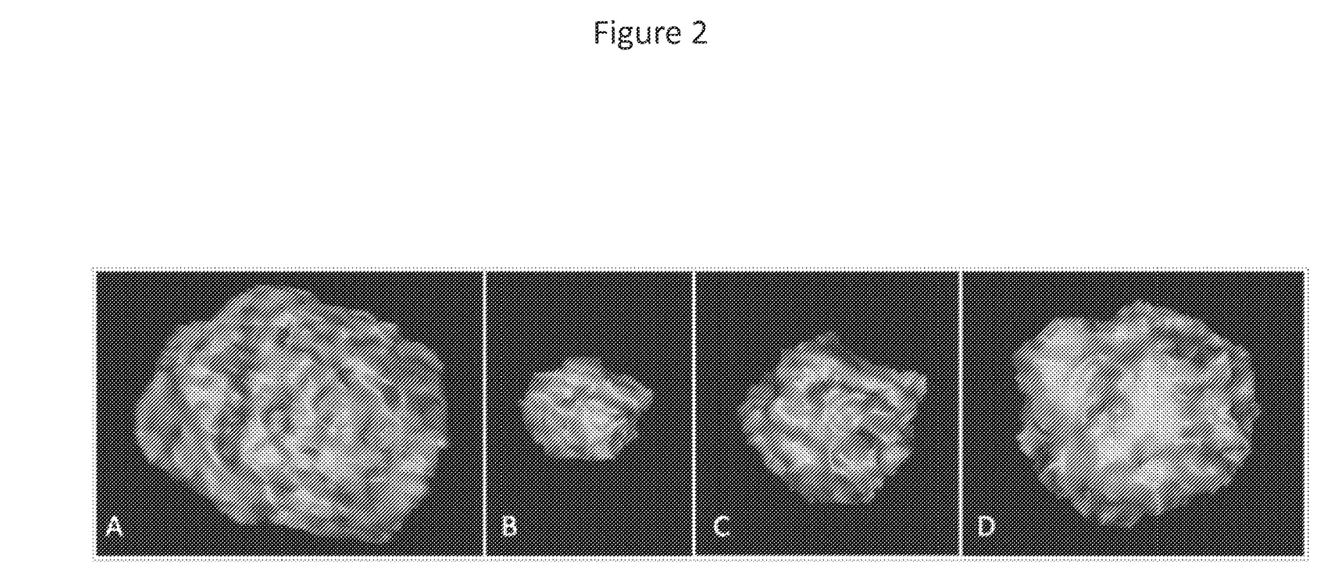
FIG. 2. A 35 year-old woman with stage IV lung adenocarcinoma with fast tumor growth.
Figure 3:
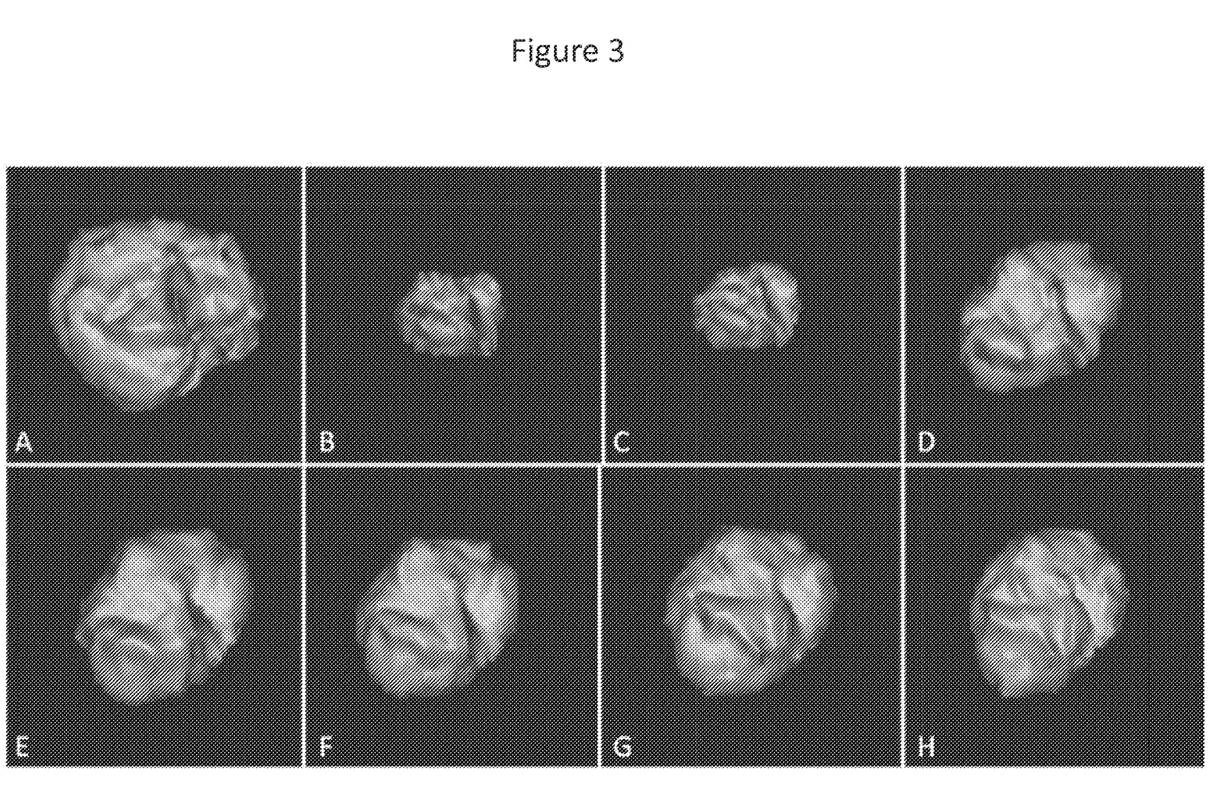
FIG. 3. A 52 year-old woman with stage IV lung adenocarcinoma with slow tumor growth.
Figure 4:
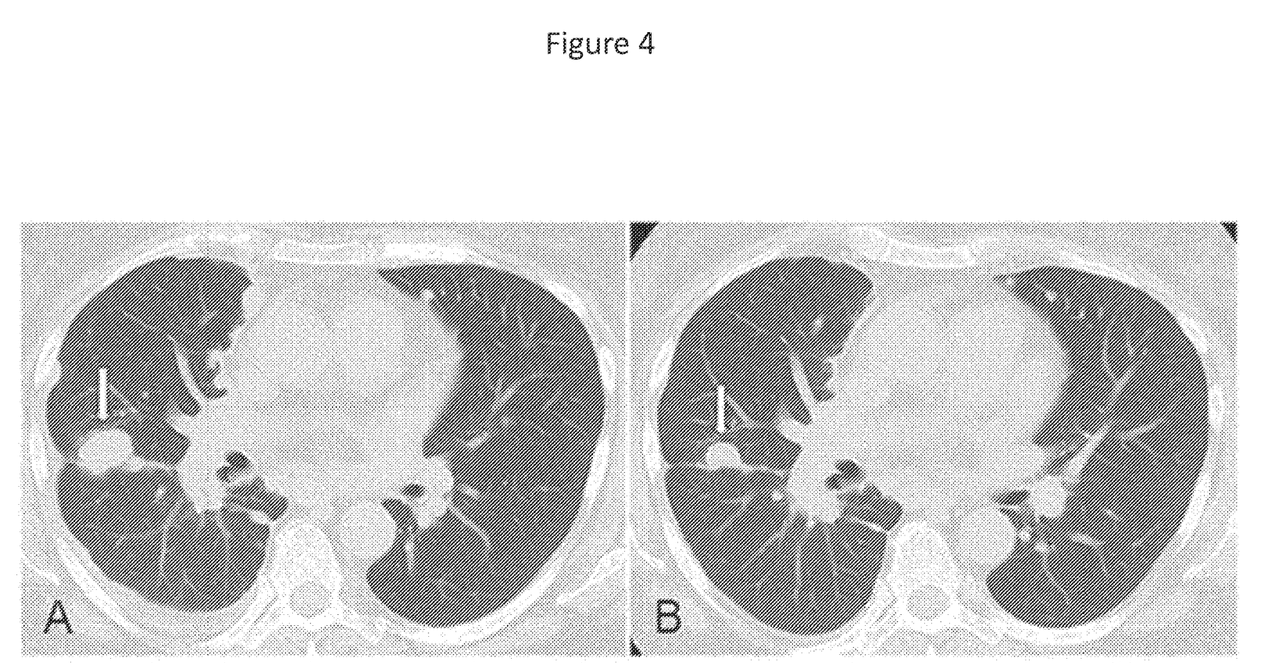
FIG. 4. A 70 year-old woman with stage IV lung adenocarcinoma

Fourteen patients (14/58, 24%) experienced the growth rate of $\log_e V > 0.15$/months on two consecutive scans, which occurred after nadir in all patients (FIGS. 2-3). The median time from baseline to the second scan with rate >0.15/months was 9.7 months (range: 3.1-20.7). The median time on TKI in these 14 patients was 11.7 months, compared to 17.9 months in 44 patients who did not experience the rate >0.15/months on two consecutive scans. In 6 of the 14 patients (43%), TKI monotherapy was terminated within a month from the second scan, with no further CT before therapy termination. The remaining 8 patients (57%) remained on TKI monotherapy beyond the $2^{nd}$ scan and had at least one additional chest CT scan while on TKI.

Example 4: Translating The Results Of Radiographic Response In EGFR-Mutant Cohort To ALK-Positive Cohort The EML4-ALK fusion oncogene, one of the newer molecular targets in NSCLC, is present in 5-7% of NSCLC [13-19]. ALK-positive NSCLC patients respond dramatically to ALK inhibitor, crizotinib, with the response rate of up to 61% in the trials, the overall disease control rates close to 90%, and the progression-free survival of 10 months [19]. In these patients, significant reduction of tumor burden is observed when they initially respond to crizotinib (FIG. 5). However, as known in EGFR-mutant NSCLC patients, ALK-positive NSCLC patients also develop resistance to crizotinib and tumors start to grow back after initial response. Presumed clinical benefit of crizotinib is noted in these patients after they experienced RECIST progression, which can lead to continuation crizotinib beyond RECIST progression [32-33]. Additional radiographic criteria should be established for ALK-positive NSCLC patients during crizotinib therapy to provide an aid for therapeutic decision making Given similarities of genomic, clinical, and radiographic behaviors of the tumors between EGFR-mutant NSCLC and ALK-positive NSCLC, it is expected that the results of radiographic assessment in EGFR-mutant NSCLC patients can be translated into a cohort of ALK-positive NSCLC patients. In addition, despite differences in molecular characteristics with different translocations, the tumoral behavior and response characteristics of ALK-positive patients are relatively homogeneous, which will facilitate the identification of meaningful volumetric response criteria. Establishing the volumetric response cut-off that can aid therapeutic decisions in ALK-positive NSCLC patients will help identifying patients who may benefit from additional or alternative therapy with other effective ALK inhibitors after 8 weeks. The study will be a leading example of translation of the research results of radiographic response assessment from one genomically-defined cohort to the other, which will further expand the utility of imaging in assessing response and guiding treatment decisions in the era of genomic medicine and personalized cancer care.

The identification of EGFR-mutant NSCLC patients since 2004 and their treatment with erlotinib or gefitinib provides the largest and longest studied genomically-defined cohort among NSCLC population. The knowledge and findings in these patients have been translated to the therapy and management of other genomically-define subsets with novel genomic abnormalities, including ALK-rearrangement, ROS-1 rearrangement and BRAF mutations. Given the successful translations the knowledge from EGFR-mutant cohort to others in the fields of clinical and translational oncology, the results of radiographic investigations of response assessment in EGFR-mutant NSCLC should also be translated into other cohorts.

We claim:

1. A method of assessing tumor growth rate in a patient receiving treatment for a tumor, the method comprising:
   a) determining the tumor volume of the tumor;
   b) determining the natural log ($\log_e$) of the tumor volume determined in step (a) to provide a patient volumetric tumor growth rate; and
   c) comparing the patient volumetric growth rate to a threshold volumetric tumor growth rate, wherein: (i) when the patient volumetric tumor growth rate is lower than the threshold volumetric tumor growth rate indicates the tumor is slow growing or (ii) when the patient volumetric tumor growth rate is higher than threshold volumetric tumor growth rate indicates the tumor is fast growing.

2. A method of providing a treatment alteration recommendation for a patient receiving treatment for a tumor, the method comprising:
   a) determining the tumor volume of the tumor at a first period of time;
   b) determining the natural log ($\log_e$) of the tumor volume determined in step (a) to provide a patient volumetric tumor growth rate at the first period of time;
   c) determining the tumor volume of the tumor at a second period of time;
   d) determining the natural log ($\log_e$) of the tumor volume determined in step (c) to provide a patient volumetric tumor growth rate at the second period of time; and
   e) comparing the patient volumetric tumor growth rates to a threshold volumetric tumor growth rate,
wherein when both patient volumetric tumor growth rates are higher than the threshold volumetric tumor growth rate indicates that the patient's treatment regimen should be altered.

3. A method of assessing the need for further prognosis tests for a patient receiving treatment for a tumor, the method comprising:
   a) determining the tumor volume of the tumor at a first period of time;
   b) determining the natural log ($\log_e$) of the tumor volume determined in step (a) to provide a patient volumetric tumor growth rate at the first period of time;
   c) determining the tumor volume of the tumor at a second period of time;
   d) determining the natural log ($\log_e$) of the tumor volume determined in step (c) to provide a patient volumetric tumor growth rate at the second period of time; and
   e) comparing the patient volumetric tumor growth rates to a threshold volumetric tumor growth rate,
wherein when both patient volumetric tumor growth rates are lower than the threshold volumetric tumor growth rate indicates no need for additional prognostic tests.

4. The method of claim 2, wherein the first period of time is after the tumor has reached nadir.

5. The method of claim 1, wherein the tumor volume is determined by a radiographic method.

6. The method of claim 5, where the radiographic method is a CT scan.

7. The method of claim 1, wherein the tumor is a solid tumor.

8. The method of claim 7, wherein the tumor is a lung tumor.

9. The method of claim 1, wherein the patient is receiving a targeted therapy for the tumor.

10. The method of claim 9, wherein the targeted therapy is based upon a tumor mutation.

11. The method of claim 10, wherein the targeted therapy is a tyrosine kinase inhibitor.

12. The method of claim 3, wherein the first period of time is after the tumor has reached nadir.

* * * * *